US00PP14320P39

(12) United States Plant Patent
McNeilage et al.

(10) Patent No.: US PP14,320 P3
(45) Date of Patent: Nov. 25, 2003

(54) KIWI PLANT NAMED 'HORTGEM WHA'

(50) Latin Name: *Actinidia arguta*
Varietal Denomination: Hortgem Wha

(75) Inventors: Mark A McNeilage, Auckland (NZ); Ron A Beatson, Motueka (NZ); Elspeth A MacRae, Auckland (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 0 days.

(21) Appl. No.: 10/119,372

(22) Filed: Apr. 8, 2002

(65) Prior Publication Data

US 2003/0196234 P1 Oct. 16, 2003

(51) Int. Cl.[7] ..... A01H 5/00

(52) U.S. Cl. ..... Plt./156

(58) Field of Search ..... Plt./156

*Primary Examiner*—Bruce R. Campell
*Assistant Examiner*—June Hwu
(74) *Attorney, Agent, or Firm*—Greenlee, Winner and Sullivan, P.C.

(57) ABSTRACT

A new and distinct kiwi plant of the species *Actinidia arguta* (Sieb & Zucc.) Planch. ex Miq. var. *arguta* is described. The variety results from a controlled pollination using a female *A. arguta* selection AA05_01 of unknown parentage and a male *A. arguta* selection AA13._0l of unknown parentage. Both named parents (AA05_01 and AA 13_01) are unpatented. The new variety is distinguished by its green hairless, edible skin, small fruit size, oblong shape and sweet aromatic taste.

8 Drawing Sheets

Genus and species of plant claimed: *Actinidia arguta.*

BACKGROUND TO THE INVENTION

Kiwi plants in cultivation are mainly varieties of *A. deliciosa*, particularly 'Hayward' although some *A. chinensis* and *A. arguta* varieties are grown. *A. deliciosa* and *A. chinensis* are closely related, whereas *A. arguta* is classified in a separate section of the genus. *A. deliciosa* and *A. chinensis* varieties have large fruit (~100 g) with hair on the skin. The main varieties in New Zealand are 'Hayward' (*A deliciosa*) and 'Hort16A' (*A. chinensis*) . Fruit are usually cut and eaten with a spoon. *A. arguta* has small fruit (~10 g) with no hair on the skin. The skin is edible so these fruit can be eaten whole, like a grape.

All Actinidia species are dioecious, so female varieties have to be interplanted with male pollinizers to ensure fruit production.

*A. arguta* vines are deciduous and tend to grow vigorously in spring and summer when rapidly-growing shoots can intertwine and tangle if not managed. Vines do best in a mild temperate climate without late spring or early autumn frosts. They produce consistent heavy crops when grown in well-drained fertile soils and given regular irrigation in dry spells.

*A. arguta* flowers in spring (late October–early December) in New Zealand. Harvest of *A. arguta* fruit may occur between early February and late March in New Zealand depending on the selection and location of plantings. Compared to *A. deliciosa* and *A. chinensis, A. arguta* fruit require more careful handling during harvest and post-harvest procedures.

SUMMARY OF THE INVENTON

The present invention is a new and distinctive kiwi plant having a small, generally oblong shaped fruit with green hairless edible skin. This new variety is designated 'Hortgem Wha' and is derived from a controlled pollination of AA05_01, a female *A. arguta* selection of unknown parentage (unpatented), with AA13_01, a male *A. arguta* selection of unknown parentage (unpatented).

The female parent arose from a seed family collected in the district Aomori, North Honshu, Japan and was introduced to New Zealand in 1977. The male parent was introduced as scionwood from The Royal Botanic Gardens, Edinburgh, Scotland to New Zealand in 1982. The provenance of both is unknown.

This new variety was created during the course of a planned plant-breeding program, which was initiated during 1987 at HortResearch in Auckland, New Zealand. The controlled cross was made in November 1987. Seeds were sown in autumn (March) 1988 and 102 seedlings from this cross were planted out in the field at HortResearch Kumeu Research Orchard in spring (October) 1988. The seedlings first fruited in February–March 1991. Twenty promising female seedlings were clonally propagated into a two-site replicated trial in 1995 and 'Hortgem Wha' (breeding code K2E5) was selected after storage and sensory evaluation in 1998.

The new variety can be asexually reproduced as cuttings or by grafting or budding on to seedling or cutting-grown rootstocks of *A. arguta*. Trial plantings as cuttings established in 1995 at TePuke and Nelson Research Centres and on seedling rootstocks established in 1998 at these sites have shown that the unique combination of characters come true to form and are established and transmitted through succeeding asexual propagations.

BRIEF DESCRIPTION OF THE ILLUSTRATIONS

Figure 1:
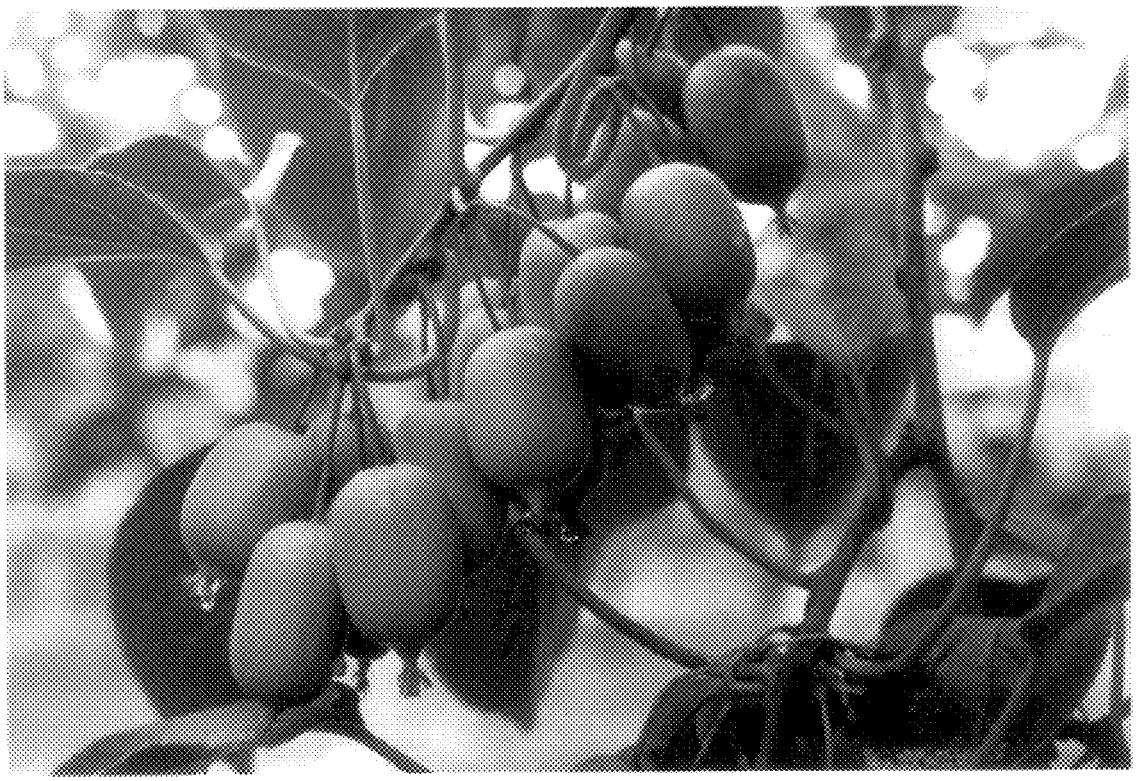
FIG. 1 shows typical fruit of the variety 'Hortgem Wha' in the orchard.
Figure 2:
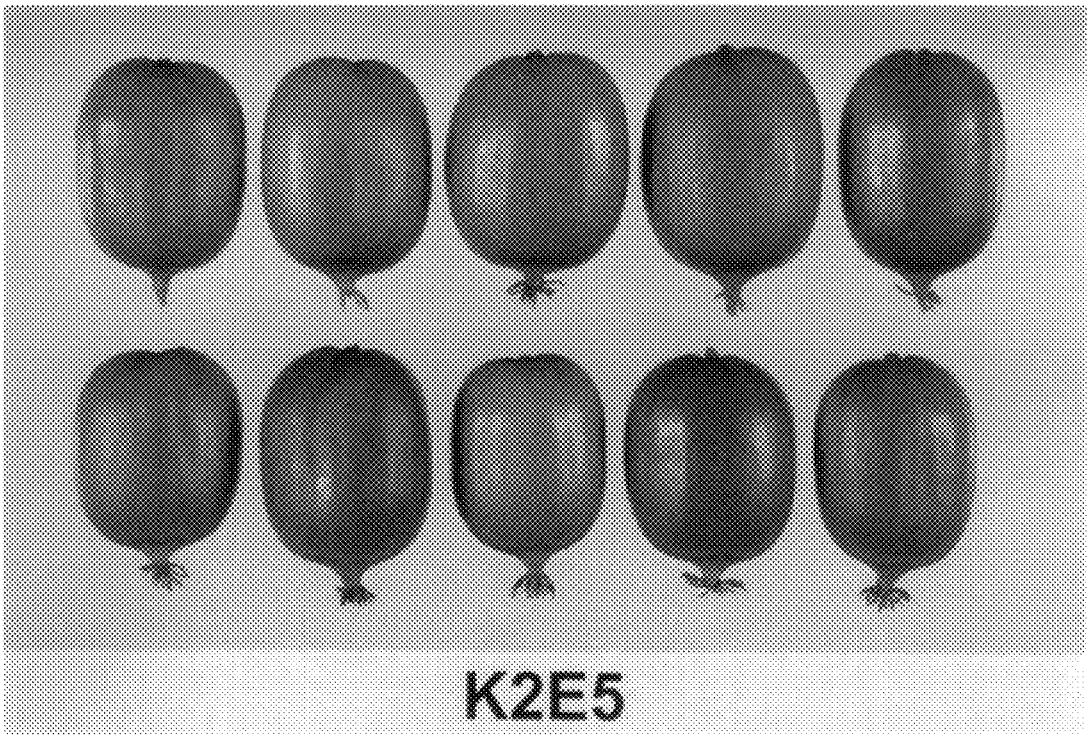
FIG. 2 shows typical fruit of the variety 'Hortgem Wha' in the studio.
Figure 3:
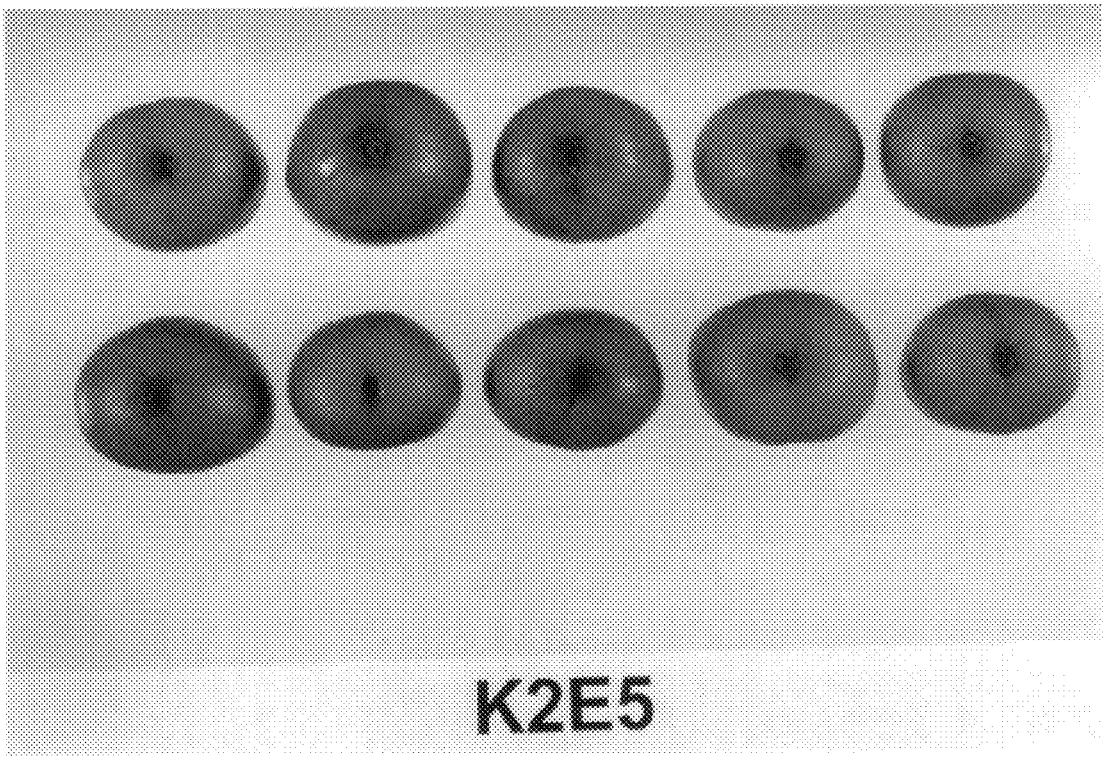
FIG. 3 shows a stem end view of 'Hortgem Wha' fruit.
Figure 4:
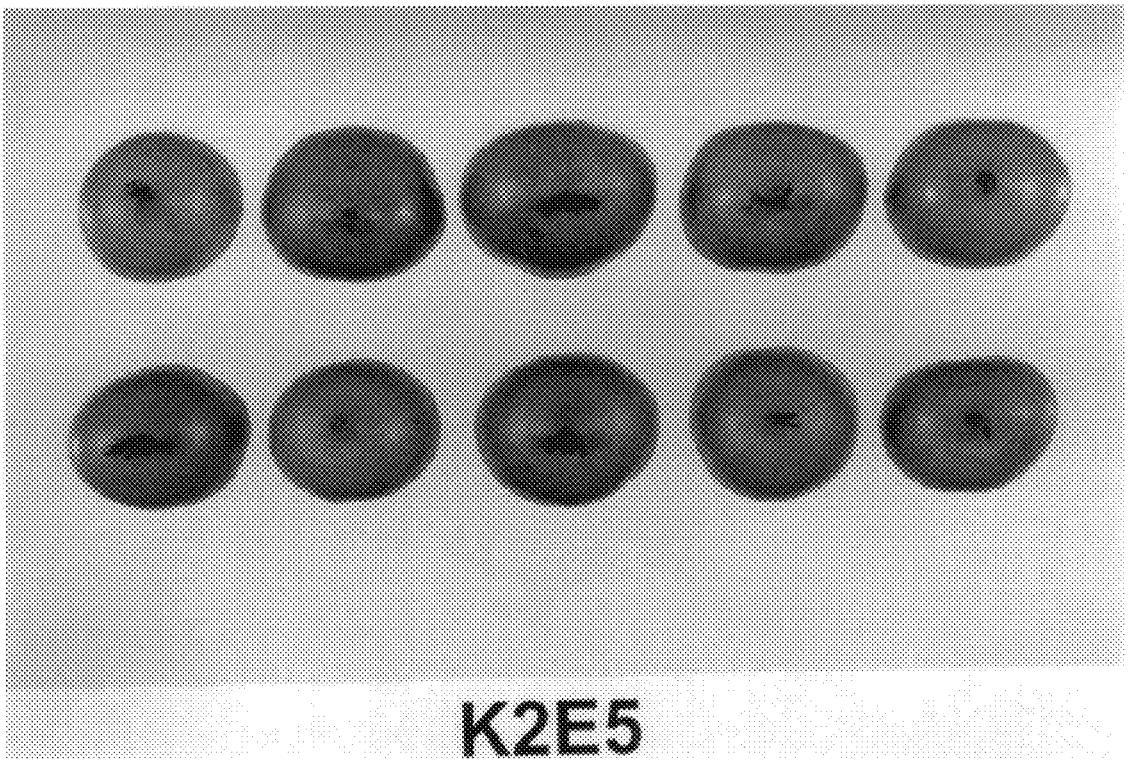
FIG. 4 shows a stylar end view of 'Hortgem Wha' fruit.
Figure 5:
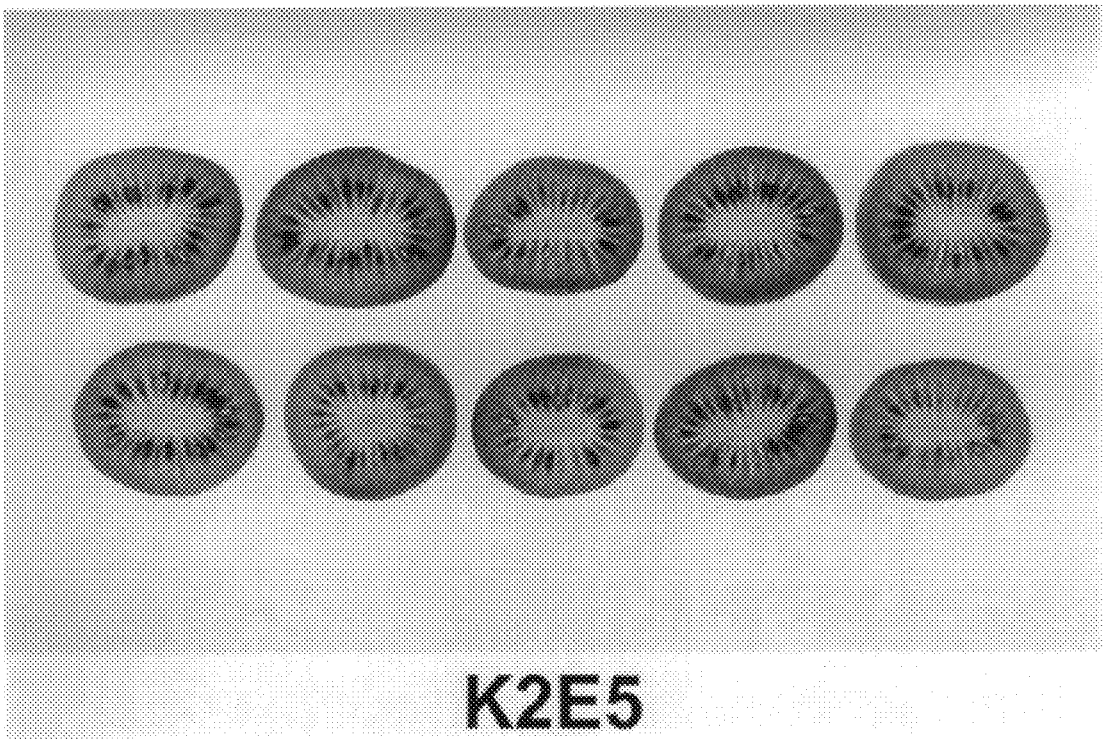
FIG. 5 shows 'Hortgem Wha' fruit in cross-section.
Figure 6:
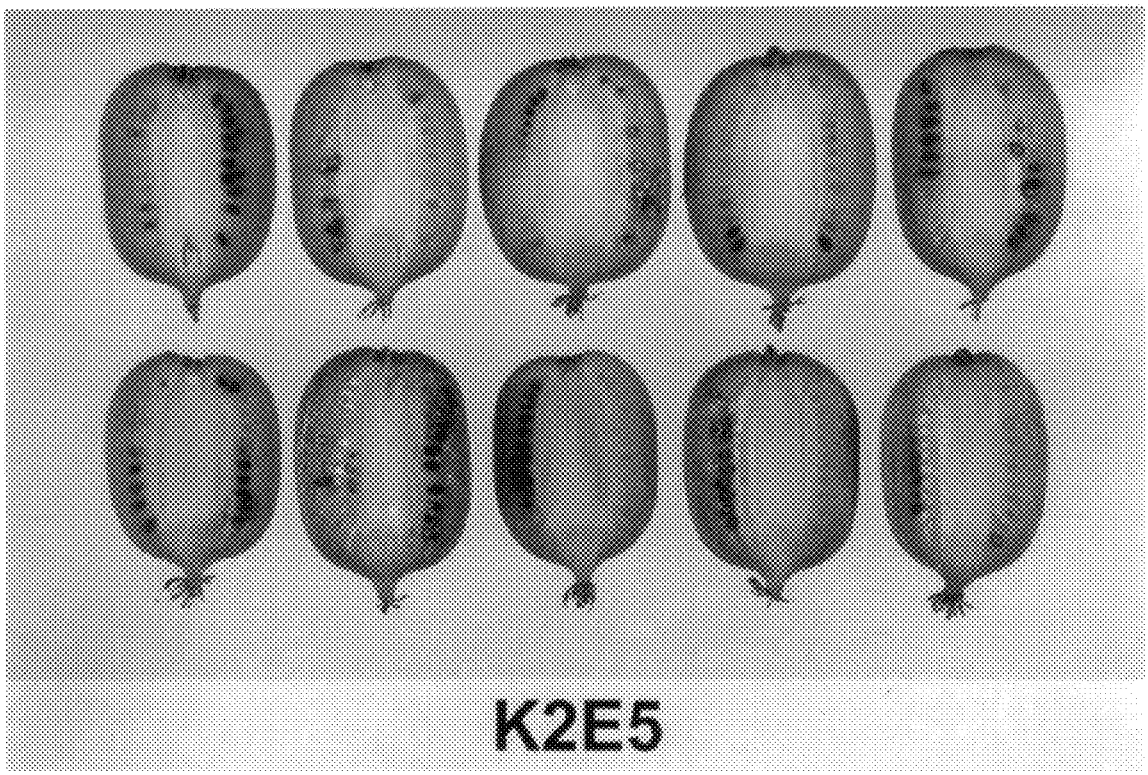
FIG. 6 shows 'Hortgem Wha' fruit in longitudinal-section.
Figure 7:
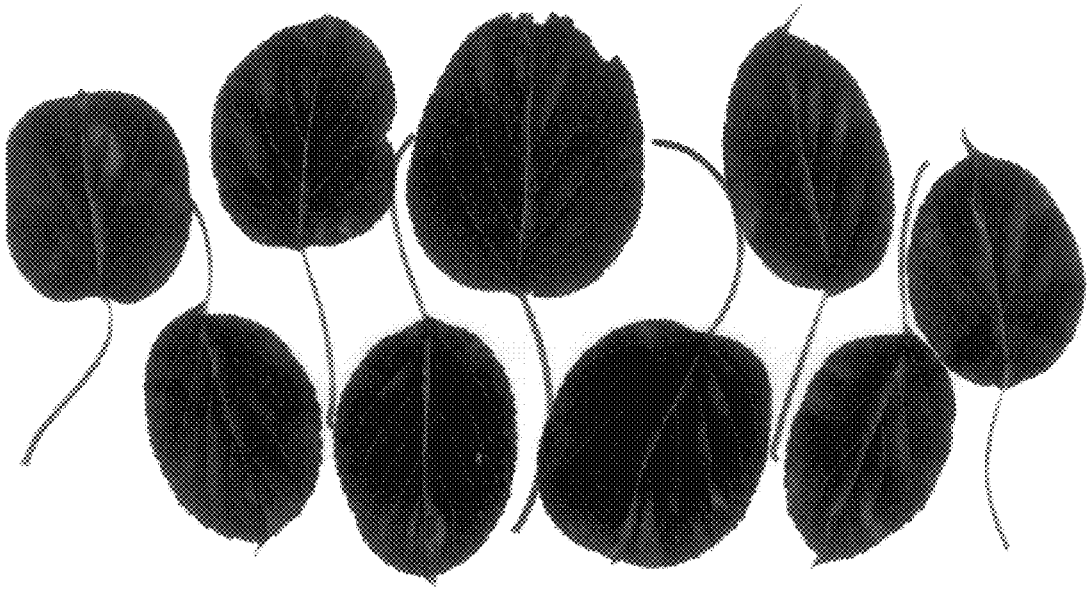
FIG. 7 shows leaves of the variety 'Hortgem Wha'.
Figure 8:
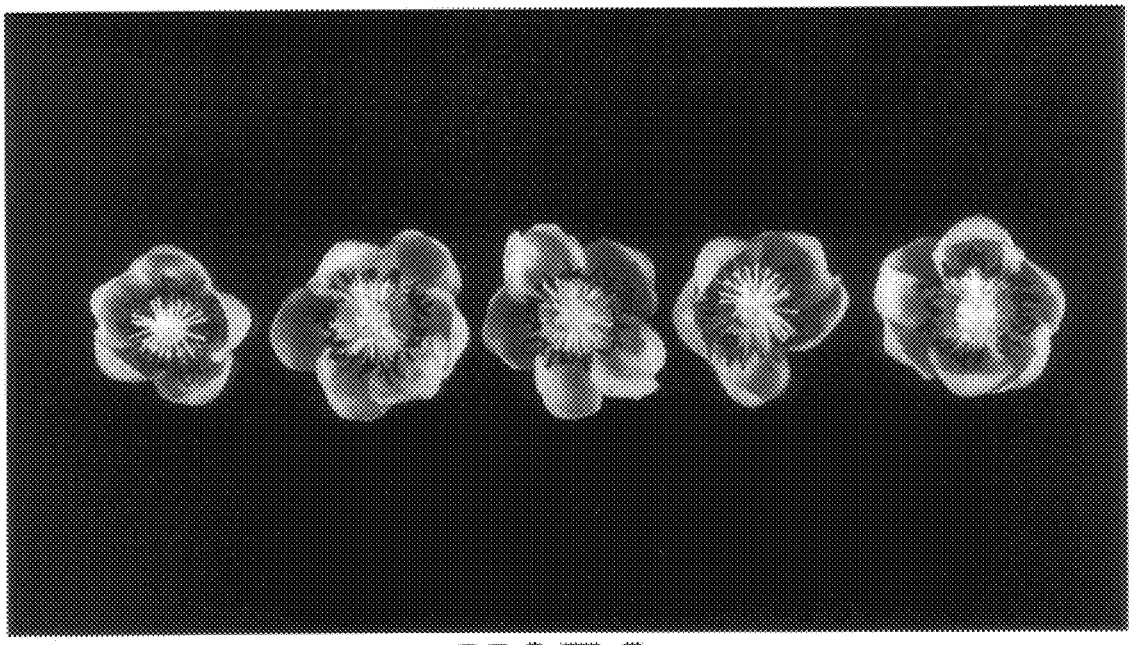
FIG. 8 shows flowers of the variety 'Hortgem Wha'.

Photographs of fruit were taken after the normal harvest date and are depicted in colors as nearly true as is reasonably possible to make the same in a color illustration of this character. Fruit skin color may vary depending upon extent of exposure to direct sunlight.

COMPARISON TO CLOSEST VARIETY

The distinctive characteristics of this new kiwi variety, described in detail below, were observed in 2001 at Te Puke, New Zealand. The plants observed were established from cuttings and were 6 years old at the time. 'Hortgem Wha' is a new variety of *A. arguta* distinctive in its own right. Comparison with another similar variety 'Hortgem Tahi' (U.S. Plant Pat. No. 13,815) showed that 'Hortgem Wha' may be distinguished as follows in Table 1.

TABLE 1

| Similar variety | Characteristic | Expression of the characteristic for the similar variety | Expression of the characteristic for the candidate variety |
|---|---|---|---|
| Hortgem Tahi | Fruit shape | spheroid | oblong |
| Hortgem Tahi | Start of harvest | late Feb. | late Feb.–early March |
| Hortgem Tahi | Storage life of fruit at 0° C. in air storage | ~10–12 weeks | ~6–8 weeks |

BOTANICAL DESCRIPTION OF THE PLANT

The new variety 'Hortgem Wha' is pistallate, with morphologically perfect but functionally imperfect flowers, i.e. the flowers produce only sterile pollen and thus require a pollinizer for fruit production. Characteristics of the new variety include a short period (~3 months) between flowering and harvest, early harvest, small oblong fruit with green hairless edible skin, green flesh and a sweet aromatic flavor.

Horticultural terminology is used in accordance with revised UPOV guidelines for kiwi. All dimensions in millimeters, weights in grams (unless otherwise stated). Where a color reference is given these refer to The R.H.S. Colour Chart, The Royal Horticultural Society, London. 3rd Edition, 1995.

Plant (Measurements from samples of 20, unless stated).
- *Sex expression.*—Female.
- *Vigour.*—Strong.

Young shoot:
- *Hairs.*—Present.
- *Density of hairs.*—Sparse.
- *Type of hairs.*—Tomentose.
- *Anthocyanin coloration of growing tip.*—Near Red 53B.
- *Anthocyanin coloration of leaf axil.*—Absent or very weak.

Stem:
- *Coloration of leaf axil.*—Absent or very weak.
- *Diameter.*—Thin; mean 9.1 (range 8.5–10.0).
- *Dormant bud diameter.*—Small, 1.2 mm (range 0.8–1.5).
- *Color on upper side of shoot.*—Greyed-Orange 166B.
- *Character of bark.*—Smooth.
- *Hairs.*—Absent.
- *Conspicuousness of lenticels.*—Conspicuous.
- *Number of lenticels.*—Many.
- *Color of lenticels.*—Near Greyed-orange 169D.
- *Size of bud support.*—4.8 (range 3.8–5.7).
- *Visibility of bud* (*dormant canes*).—Visible.
- *Number of hairs visible on bud*(*dormant canes*).—Absent.
- *Leaf scar.*—Deep.

Leaf (mature):
- *General shape of blade.*—Ovate/broad ovate.
- *Length.*—115.4 mm (range 101–131).
- *Width.*—68.4 mm (range 57–84).
- *Petiole length.*—53.5 mm (range 43–73).
- *Shape of tip of blade.*—Caudate.
- *Shape of base of blade.*—Rounded.
- *Arrangement of leaf bases.*—Far apart.
- *Puckering/blistering on upper side of blade.*—Absent or very weak.
- *Margin.*—Ciliate.
- *Green color of upper side of blade.*—Medium.
- *Glossiness of upper surface of blade.*—Medium.
- *Color of lower side of blade.*—Light green.
- *Glaucosity* (*lower side of blade*).—Absent.
- *Hairs on petiole.*—Absent or very weak.
- *Density of hairs on petiole.*—Absent or very sparse.
- *Anthocyanin coloration on upper side of petiole.*—Near Red 53A.

Flower:

Inflorescence:
- *Predominant number of flowers.*—Three.

Pedicel:
- *Length.*—Short 28.1 mm (range 20.6–33.7).
- *Hairs.*—Sparse.
- *Length of hairs.*—Very short.

Flower:
- *Number of sepals.*—5.8 (range 5–7).
- *Color of sepals.*—Within the range near Red 53B to Grey-brown 199D.
- *Diameter* (*terminal or king flower when fully open*).—Small 28.2 (range 26.3–30.6).
- *Petal length.*—15.1 (range 13.3–17.1).
- *Petal width.*—10.3 (range 8.7–12.4).
- *Petal length/width ratio.*—1.5 (range 1.12–1.84).
- *Mean number of petals per flower.*—6.1 (range 5–7).
- *Number of flowers with more than six petals.*—6 out of 20 (4 with 5, 10 with 6).
- *Arrangement of petals.*—Overlaping.
- *Primary color of petals* (*when fully open*).—Near Green white 157A.
- *Type of coloration of petals.*—Uniform over entire petal.
- *Number of stamens.*—44.4 (range 36–49).
- *Length of stamen filaments.*—4.2 (range 3.5–4.7).
- *Length of anthers.*—2.4 (range 2.1–2.6).
- *Filament color.*—Near Green 130D.
- *Anther color.*—Near Black 202A.
- *Style number.*—23.8 (range 21–28).
- *Length of styles.*—3.7 (range 3.0–4.2).
- *Attitude of styles.*—Semi-erect.

*Curvature of styles.*—Weak.
*Length of ovary.*—7.9 (range 7.2–8.5).
*Amount of hair on ovary.*—Absent.
*Color of ovary.*—Near Yellow green 145A.

Fruit:
*Overall size.*—8.5 g (range 7.4–11.4).
*Length.*—32.0 mm (range 30–40).
*Width (max).*—23.3 mm (range 21–26).
*Width (min).*—19.7 mm (range 18–22).
*Core diameter (max).*—8.6 mm (range 6–12).
*Core diameter (min).*—4.2 mm (range 3–5).
*Locule number.*—23.6 (range 19–27).
*Peduncle length.*—27.9 mm (range 20–36).
*Peduncle width.*—1.7 mm (range 1.3–2.3).
*General shape.*—Oblong.
*Cross section at median.*—Oblate.
*General shape of stylar end.*—Slightly pointed protruding.
*Shape of shoulder on stalk end.*—Square.
*Skin color at harvest (fruit still hard).*—Medium green.
*Skin color change during ripening.*—Medium green.
*Skin color at maturity for consumption.*—Medium green.
*Hairs.*—Absent.
*Core shape (in cross section).*—Transverse elliptic.
*Core woody spike.*—Absent.
*Outer pericarp color at maturity for consumption.*—Green.
*Inner pericarp col. (locules) at mat. for consumption.*—Green.
*Core color at maturity.*—Green white.
*Brix level at maturity for consumption.*—17% .
*Seed color at maturity (in flesh).*—Dark red brown.
*Seed color when dry.*—Red brown.

Events:
*Time of vegetative budbreak.*—Early–mid September.
*Time of beginning of flowering.*—Early–mid November.
*Time of maturity for harvest.*—Late February – early March.

Fruit:
*Outer pericarp color at maturity for consumption.*—Within the range near Green 139B to 141 B.
*Inner pericarp col. (locules) at mat. for consumption.*—Within the range near Green 139B to 141 B.
*Core color at harvest.*—Within the range near Yellow-green 154D to Green-white 157C.
*Seed color (in flesh).*—Within the range near Greyed-orange 172B to 175C.
*Seed color (dry seed).*—Within the range near Greyed-orange 172B to 175C.
*Skin color at maturity.*—Within the range near Green141 A to 143A.

Leaf:
*Color of upper side (in mature leaf after petal fall).*—Within the range near Green 136A to 139A.
*Color of lower side (in mature leaf after petal fall).*—Within the range near Green 138A to 141A.

Flower:
*Color of main body of petals.*—Near Green-white 157A.
*Color of ovary.*—Near Yellow-green 145A.

Plant stem:
*Color on exposed side.*—Within the range near Greyed-orange 166B to 176A.

HORTICULTURAL CHARACTERISTICS

Details below relate to observations made on cutting-grown plants growing at HortResearch Te Puke Research Centre, New Zealand. These vines were 3 years old.

Cropping: Young vines of 'Hortgem Wha' are precocious, beginning to bear in their second year and are expected to reach full capacity at about 7 years. The storage life of 'Hortgem Wha' fruit is 6–8 weeks at 0° C., if stored in unventilated containers in air storage.

Yield and fruit size: (Data from harvesting all fruit from 8 vines in early March 1999).

Mean fruit weight: 7.34 g Maximum: 7.85 g Minimum: 6.53 g.

Mean fruit number: 845 Maximum: 1,498 Minimum: 297.

Mean yield: 6.2 kg Maximum: 11.1 kg Minimum: 2.3 kg.

It is anticipated mature, well-managed vines would yield approximately 5000 fruit per vine with a mean fruit weight of 10 g and mean yield per vine of 50 kg.

No pest and disease resistance has been observed. The plant hardiness range (according to the American zone classification) has not been determined. Under New Zealand conditions, the plants are grown in areas that experience some winter cold and frost, estimated to be equivalent to the minimum temperature range of zones 8 and 9.

What is claimed is:

1. A new and distinct kiwi plant of the species *A. arguta* substantially as herein described and illustrated, characterized by small oblong fruit with green hairless edible skin and green flesh with a sweet aromatic flavor.

* * * * *

K2F5

K2E5